(12) United States Patent
Vincent et al.

(10) Patent No.: US 7,767,966 B2
(45) Date of Patent: Aug. 3, 2010

(54) METHOD AND APPARATUS FOR DETECTING ORGANIC MATERIALS AND OBJECTS FROM MULTISPECTRAL REFLECTED LIGHT

(75) Inventors: Robert Vincent, Bowling Green, OH (US); B. B. Maruthi Sridhar, Bowling Green, OH (US)

(73) Assignee: Bowling Green State University, Bowling Green, OH (US)

( * ) Notice: Subject to any disclaimer, the term of this patent is extended or adjusted under 35 U.S.C. 154(b) by 57 days.

(21) Appl. No.: 12/214,697

(22) Filed: Jun. 20, 2008

(65) Prior Publication Data

US 2009/0314942 A1     Dec. 24, 2009

(51) Int. Cl.
*G01J 5/02* (2006.01)
(52) U.S. Cl. .............................. 250/339.01; 250/339.11
(58) Field of Classification Search ............ 250/339.01, 250/339.11
See application file for complete search history.

(56) References Cited

U.S. PATENT DOCUMENTS

| | | |
|---|---|---|
| 4,217,490 A | 8/1980 | Fiorito et al. |
| 4,847,854 A | 7/1989 | Van Dijk |
| 4,953,972 A | 9/1990 | Zuk |
| 4,965,442 A | 10/1990 | Girod et al. |
| 4,989,084 A | 1/1991 | Wetzel |
| 5,003,166 A | 3/1991 | Girod |
| 5,012,675 A | 5/1991 | Koller et al. |
| 5,359,681 A | 10/1994 | Jorgenson et al. |
| 5,530,551 A | 6/1996 | Cantrall et al. |
| 5,582,369 A | 12/1996 | Blancke |
| 5,647,030 A | 7/1997 | Jorgenson et al. |
| 5,703,623 A | 12/1997 | Hall et al. |
| 5,835,645 A | 11/1998 | Jorgenson et al. |
| 5,841,570 A | 11/1998 | Velsko |
| 5,892,585 A | 4/1999 | Lianza et al. |
| 5,926,773 A | 7/1999 | Wagner |
| 6,008,492 A | 12/1999 | Slater et al. |
| 6,026,821 A | 2/2000 | Last |
| 6,035,246 A | 3/2000 | Wagner |
| 6,133,997 A | 10/2000 | Yamawaki et al. |
| 6,184,981 B1 | 2/2001 | Hasson et al. |
| 6,285,630 B1 | 9/2001 | Jan |
| 6,307,500 B1 | 10/2001 | Cornman et al. |
| 6,347,762 B1 | 2/2002 | Sims et al. |
| 6,348,699 B1 | 2/2002 | Zehe |
| 6,370,260 B1 | 4/2002 | Pavlidis et al. |
| 6,422,508 B1 | 7/2002 | Barnes |
| 6,456,991 B1 | 9/2002 | Srinivasa et al. |
| 6,495,363 B2 | 12/2002 | Bogdanov |
| 6,495,818 B1 | 12/2002 | Mao |
| 6,504,943 B1 | 1/2003 | Sweatt et al. |
| 6,536,948 B1 | 3/2003 | Vivekanandan et al. |
| 6,556,297 B1 | 4/2003 | Cappiello |
| 6,570,652 B1 | 5/2003 | Cappiello |

(Continued)

*Primary Examiner*—David P Porta
*Assistant Examiner*—Mindy Vu
(74) *Attorney, Agent, or Firm*—Roger A. Gilcrest (57) ABSTRACT

The present invention is a method of determining the presence of keratin, particularly hard keratin, such as exists in mammalian hair and feathers, and objects comprising such materials. The method of the present invention also includes displaying information derived from such a determination, as well as a measurement method followed by transmission of data to a remote processing site for analysis or display. The invention also includes devices for carrying out the determination, display and/or transmission.

29 Claims, 5 Drawing Sheets

U.S. PATENT DOCUMENTS

| | | |
|---|---|---|
| 6,608,931 B2 | 8/2003 | Sunshine et al. |
| 6,610,983 B2 | 8/2003 | Toomey |
| 6,621,958 B1 | 9/2003 | Dueck et al. |
| 6,633,037 B2 | 10/2003 | Toomey |
| 6,731,838 B1 | 5/2004 | Dueck et al. |
| 6,734,966 B2 | 5/2004 | McCarthy |
| 6,741,408 B2 | 5/2004 | Beattie et al. |
| 6,741,740 B2 | 5/2004 | Sunshine et al. |
| 6,763,136 B1 | 7/2004 | Sweet |
| 6,771,798 B1 | 8/2004 | Haas et al. |
| 6,778,702 B1 | 8/2004 | Sweet |
| 6,804,400 B1 | 10/2004 | Sharp |
| 6,812,846 B2 | 11/2004 | Gutta et al. |
| 6,819,798 B2 | 11/2004 | Gorin |
| 6,829,370 B1 | 12/2004 | Pavlidis et al. |
| 6,841,781 B2 | 1/2005 | Toomey |
| 6,937,885 B1 | 8/2005 | Lewis et al. |
| 6,940,999 B2 | 9/2005 | Lin |
| 6,958,812 B1 | 10/2005 | Videen |
| 6,963,400 B1 | 11/2005 | Videen |
| 6,998,614 B2 | 2/2006 | Lanoue |
| 7,004,911 B1 | 2/2006 | Tu et al. |
| 7,009,550 B2 | 3/2006 | Moeller-Jensen |
| 7,013,172 B2 | 3/2006 | Mansfield et al. |
| 7,027,773 B1 | 4/2006 | McMillin |
| 7,076,088 B2 | 7/2006 | Pavlidis |
| 7,085,416 B2 | 8/2006 | Sunshine et al. |
| 7,149,366 B1 | 12/2006 | Sun |
| 7,153,299 B1 | 12/2006 | Tu et al. |
| 7,173,534 B1 | 2/2007 | Markham et al. |
| 7,194,111 B1 | 3/2007 | Schaum et al. |
| 7,221,798 B2 | 5/2007 | Sunshine et al. |
| 7,223,047 B2 | 5/2007 | Prevost |
| 7,248,358 B2 | 7/2007 | Geshwind et al. |
| 7,253,748 B2 | 8/2007 | Nitzan et al. |
| 7,265,826 B2 | 9/2007 | Mottin |
| 7,282,715 B2 | 10/2007 | Barron |
| 7,295,925 B2 | 11/2007 | Breed et al. |
| 7,297,154 B2 | 11/2007 | Tu et al. |
| 7,301,636 B2 | 11/2007 | Jung et al. |
| 7,477,309 B2 | 1/2009 | Cuccias |
| 2004/0039298 A1 | 2/2004 | Abreu |
| 2005/0209514 A1* | 9/2005 | Oshima et al. ............. 600/310 |
| 2007/0161877 A1 | 7/2007 | Arai et al. |
| 2007/0195646 A1 | 8/2007 | Govindswamy et al. |
| 2008/0111074 A1 | 5/2008 | Weir et al. |

* cited by examiner

Figure 1

Figure 2. Spectra of mammal hair from the backs of a yellow Labrador retriever dog, two cats (one blonde and one black), and a human blonde head of hair, with added spectra of tail feathers from a grouse (orange) and wing feathers from a woodcock (brown), which are game birds.

METHOD AND APPARATUS FOR DETECTING ORGANIC MATERIALS AND OBJECTS FROM MULTISPECTRAL REFLECTED LIGHT

BACKGROUND OF THE INVENTION

The present invention relates to a method of detecting hard keratin (mammalian hair, feathers, etc.) from reflected light.

In many instances it is desirable to be able to detect the presence of hard keratin (mammalian hair, feathers, etc.) in an area, particularly in areas where it is desirable to be able to determine the presence of organic materials comprising or made from hard keratin (mammalian hair, feathers, etc.).

It is particularly desirable to be able to detect the presence of hard keratin (mammalian hair, feathers, etc.) in a manner that is convenient and provides relatively immediate results so that an operator may take action in any one of several applications for the present invention.

It is also desirable to be able to signal an operator in a manner that would allow an operator to be aware of such detection.

In many instances it would be beneficial to be able to visualize the results of such detection in order that an operator may visually identify organic material objects comprising or made from hard keratin (mammalian hair, feathers, etc.).

In addition to the features mentioned above, objectives and advantages of the present invention will be readily apparent upon a reading of the following description and through practice of the present invention.

SUMMARY OF THE INVENTION

In general terms, the present invention includes a method of determining the presence of keratin, particularly hard keratin, such as exists in mammalian hair and feathers, and objects comprising such materials. The method of the present invention optionally includes displaying information derived from such a determination, as well as a measurement method followed by transmission of data to a remote processing site for analysis or display.

The present invention relates to a method of detecting and/or imaging hard keratin, such as found in mammalian hair or feathers from reflected light, and also includes devices for the measurement, calculation and transmission of data relating to that method, and for the display of images from that data. The invention also includes devices for carrying out the determination, display and/or transmission of related data or images, and to take action in response thereto (such as through signals, alarms, etc.).

The present invention may also include determination of the presence of hard keratin through the determination of spectral features in the near or short wave infrared wavelength region, such as local reflectance minimum or minima, or any combination of local reflectance maximum/maxima and/or local reflectance minimum/minima, which are able to be the basis of the determination of the presence of hard keratin, and the display of images comprising hard keratin. The method of the present invention provides the means of locating materials of a character that indicates mammalian origin, accurately determining their spatial location and extent.

In a preferred embodiment, the identification of a material is made by determining from its surface spectral reflectance properties the existence of representative reflectance maximum/maxima in the near or short wave infrared wavelength regions. This may be taken from a scene so as to distinguish such materials from other materials not of this character or background. The determination of spatial location and extent is/may be by the rapid collection of spectral measurements (nominally tens of thousands per second) in the form of an image and the reference of this image with GPS position to very high accuracy. Target identification and geolocation may be computed in near realtime or realtime. The present invention also includes devices for performing the method.

General Method of Detecting Organic Material from Reflected Light Method with Passive Light The method comprises the steps of: (a) sensing with a sensor unit reflected light in the near infrared wavelength region from objects in an area; and (b) determining whether at least one object comprising hard keratin (mammalian hair, feathers, etc.) is present in the area based upon the identification of at least one local absorbance maximum or minimum in the near infrared wavelength region that is indicative of the presence of hard keratin (mammalian hair, feathers, etc.).

This may be done for instance by application of an algorithm to reflected light of wavelengths at, and above and/or below the at least one local absorbance maximum or minimum in the near infrared wavelength region. In reflectance measurements, absorptivity at a given wavelength or wavelength region appears as a local maximum while reflectivity appears as a local maximum.

As used herein, the near infrared wavelength region is the wavelength region from about 1350 to about 2350 nanometers. This region includes the short wave infrared (SWIR) region.

An example of an algorithm to determine the presence of a local absorbance minimum or maximum is carried out through use of a three-band ratio of $(B1+B3)/[2*(B2)]$ wherein $B2$ is the detected radiance of light at a wavelength (or within a wavelength sub-region) coming from the object, and at a wavelength where the spectral reflectance (or spectral absorption) forms a local minimum (or local maximum), and $B1$ and $B3$ are the corresponding detected radiance of light at a wavelength (or within a wavelength sub-region) coming from the object at a wavelength where the spectral reflectance (or spectral absorption) forms a local maximum (or local minimum) respectively above and below the $B2$ wavelength (or wavelength sub-region center). In the case of wavelength sub-regions, these values typically are those centered respectively above and below the $B2$ wavelength region. This ratio value will be $>1.0$ because reflectance measured at $B2$ is at or very near a local spectral reflectance minimum (i.e., a local absorbance maximum) as compared to $B1$ and $B3$, and $<1.0$ if absorbance is measured (in transmission, rather than reflection) at $B2$ (i.e., a local reflectance minimum) as compared to $B1$ and $B3$. Similar corresponding analyses may be made depending upon whether one is seeking to identify one or local absorbance maxima or minima in any reflectance or transmission spectra. That is, while use of reflectance data is preferred, the present invention is not limited to this type of spectra as one may likewise be able to use absorbance measurements to obtain the same or similar results.

Depending upon the nature of the targeted maximum or minimum, one will typically locate the $B1$ and $B3$ wavelength positions (or where sub-regions are used, wavelength region centers) at a spectral distance of about $\pm 10$ nm to about $\pm 50$ nm from the targeted maximum or minimum spectral position in order to obtain an accurate indication (the three-band ratio value being $>1.0$) of the presence of that targeted local maximum or minimum. If the three spectral bands $B1$, $B2$, and $B3$ are all the same bandwidth ($\Delta\lambda$), only a slight calibration will make the value of the three-band ratio equal to 1.0, which can be calibrated by pointing the sensor toward convenient, non-keratin-rich objects in the scene, such as cement or the sky.

It will be understood that any one or more algorithms may be used to determine the presence of at least one local spectral reflectance maximum or minimum in the near infrared wavelength region, or other distinctive spectral characteristics in the spectral curve at various wavelengths or wavelength intervals of interest within an identified portion of the reflectance spectrum (a plot of spectral reflectance versus wavelength), such as by determining the sign or degree of slope in an identified spectral region (such as just shorter or just longer wavelengths than a local reflectance maximum or minimum of interest).

The results may be expressed in any way understandable to the operator or beneficiary of the detection. The results may give rise to an alarm or other signal or transmission to indicate the presence of the detected substance, such as setting off the alarm if the three-band ratio value exceeds some threshold value (like 1.1 if errors of commission are deemed less important than errors of omission, 1.4, or higher if errors of commission are deemed more important than errors of omission).

In a preferred embodiment, the at least one reflectance maximum and/or minimum is in the wavelength range of from about 1400 nanometers to about 2300 nanometers. In a more preferred embodiment, the at least one absorbance maximum and/or minimum may be selected from one or more of the following:

| Wavelength (nanometers range) | Spectral Feature Type |
|---|---|
| 1500 ± 50 | Maximum |
| 1650 ± 50 | Minimum |
| 1725 ± 50 | Maximum |
| 1850 ± 50 | Minimum |
| 1900 ± 50 | Maximum |
| 1950 ± 50 | Minimum |
| 2000 ± 50 | Maximum |
| 2050 ± 50 | Minimum |
| 2125 ± 50 | Maximum |
| 2175 ± 50 | Minimum |
| 2250 ± 50 | Maximum |

In a more preferred embodiment, the at least one absorbance maximum and/or minimum may be selected from one or more of the following:

| Wavelength (nanometers range) | Spectral Feature Type |
|---|---|
| 1500 ± 50 | Maximum |
| 1650 ± 50 | Minimum |
| 1725 ± 50 | Maximum |
| 1850 ± 50 | Minimum |

It will be appreciated that the method of the present invention may involve the detection of one or more maxima only, one or more minima only, or any combination of one or more maximum or minimum.

It is further preferred that the determination step includes identifying at least two, three, four or up to as many as 10 or more local reflectance maxima and/or minima in the near infrared wavelength region that collectively are indicative of the presence of hard keratin (mammalian hair, feathers, etc.). The greater the number of local reflectance maxima and/or minima detected, the greater may be the specificity of the detection.

In another embodiment, the determination generates data, and the method may additionally comprise displaying the data in a visual display, such as in graphically or in representational form, so as to allow one to identify any objects in the area that comprise hard keratin (mammalian hair, feathers, etc.). In this same regard, a split display may be used to display active response so as to distinguish it from inactive/background.

In the preferred embodiment, the measurement of reflected light may also involve the use of one or more filters adapted to filter the light in the near infrared wavelength region so as to filter out light of wavelengths not in the wavelength region of interest wherein the at least one absorbance maxima or minima occur. For instance, the filter(s) may be adapted to filter the light in the near infrared wavelength region so as to filter out light of wavelengths not in at least one of the following ranges of interest:

| Wavelength (nanometers range) |
|---|
| 1500 ± 50 |
| 1650 ± 50 |
| 1725 ± 50 |
| 1850 ± 50 |
| 1900 ± 50 |
| 1950 ± 50 |
| 2000 ± 50 |
| 2050 ± 50 |
| 2125 ± 50 |
| 2175 ± 50 |
| 2250 ± 50 |

It may be additionally preferred to more discretely filter the light such that the ranges given above may be ±20, ±10, or even ±5 nanometers, depending upon the desired focus of the determination.

Preferably the at least one absorbance maximum or minimum occur in the wavelength range of from about 1350 to about 2350 nanometers.

It will also be appreciated that the at least one absorbance maximum or minimum may be determined by determining amounts of reflected light from individual ranges of wavelengths. For instance, should one desire to determine an absorbance maximum at 1500 nanometers, one could perform the necessary calculation to determine the presence of a reflectance maximum by using the sum of reflected light from individual ranges of wavelengths such as that from 1470±10 nanometers (i.e., 1460-1480 nanometers), 1500±10 (i.e., 1490-1510 nanometers) nanometers and 1530±10 (i.e., 1520-1540 nanometers).

As an example, a device in accordance with the present invention may use at least 3 filters to filter the light so as to sense the reflected light discretely from the wavelengths (or wavelength ranges) available. For imaging, the sampling rate should be sufficiently fast such that measurements of absorbance or reflectance at the chosen wavelengths (or wavelength ranges) from input through processing to output may be used to create a discernable image in apparent real time. Such an input-output (frame rate) preferably should be at least 30 frames per second, or each frame (one image of the scene) should be produced in no more than 1/30 second, or about 33 milliseconds.

The filters used in the present invention may be of any type adapted to carry out the filtering requirements of the system and method of the present invention as applied. Examples include electronic filters, grating filters, and spinning wheel (rotating) filters. Commercially available filters that may operate within the near infrared range of interest include those commercially available under the VariSpec name from Cambridge Research & Instrumentation, Inc. of Woburn, Mass.

In addition to the multispectral identification and imaging methods and systems of the present invention, the method of the present invention may additionally comprise detecting the heat signature of objects in the area, and reporting or displaying this data as well, such as by displaying the heat signature of the objects in the assayed area. This also may be done by combining the display data so as to present images of objects so as to allow one to distinguish among and between objects that comprise keratin (in accordance with the present invention), those that present various heat signatures. For instance, the display may present keratin-containing objects without heat signature in one color, keratin-containing objects with heat signature in another color, and non-keratin-containing objects with heat signature in yet another color, such that the viewer could distinguish within the display field the difference between living or otherwise hot or heated objects and whether such objects are keratin containing or not. This would allow one to distinguish between, for instance, living or dead animals based upon heat signature and keratin signature, a clothed individual wearing material comprising keratin (i.e. a moving object with little or no heat signature owing to protective clothing, but comprising keratin (i.e. hair or the clothing itself if made of keratin, such as wool)). For instance, the keratin-containing objects or portions thereof could be made to appear as green, heat signatures to appear as red, and objects having both a heat signature and a hard keratin signature to appear as yellow (red and green equally combined yield yellow).

This combined display may be produced with known data display protocols, techniques and devices as known in the art.

Method with Active Light Source

The method of the present invention may also use an active light source as well as ambient light. In such cases, the method may be described as comprising the steps of: (a) exposing an area with a light source, the light source emitting light in the near infrared wavelength region; (b) sensing reflected light from the area (such as with a sensor unit); and (c) determining whether hard keratin (mammalian hair, feathers, etc.) is present in the area based upon the identification of at least one absorbance maximum or minimum in the near infrared wavelength region that is indicative of the presence of hard keratin (mammalian hair, feathers, etc.).

Figure 2:
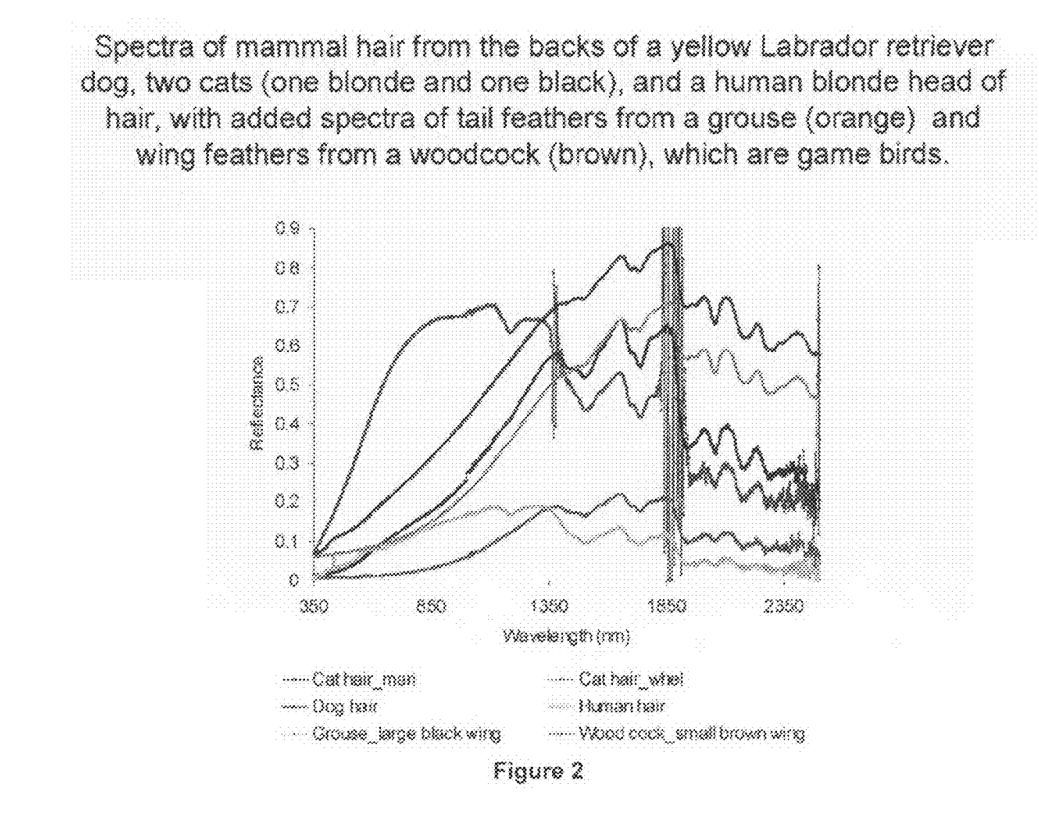
FIG. 2 is a graph of reflectance versus wavelength showing the spectra of hard keratin (mammalian hair, feathers, etc.) from a variety of sources, as may be applied in accordance with one embodiment of the present invention.

The method according to the present invention may also include a determination of whether the hard keratin is that of mammalian hair or feathers by virtue of being able to distinguish the relative absorbance (or relative reflectance) of each material at one or more wavelength values or wavelength sub-regions, as can be appreciated by the relative absorbance of each type of material in FIG. 2, which shows the reflectance spectra plots of animal hair and bird feathers. This may be done by use of an algorithm that compares the relative absorbance (or reflectance) of each material at one or more wavelength values or wavelength sub-regions by comparison to known absolute or relative spectral values or the shape of the spectra within specific sub-regions. For instance, the difference of the relative amount of reflectivity of bird feathers to that of mammalian hair is distinctly different in the spectra of FIG. 2, in the spectral region between about 1350 and 2350 nanometers.

The present invention may additionally comprise the step of generating a report of the presence of hard keratin (amount of hard keratin (mammalian hair, feathers, etc.) in the assayed area or region. This may be done using electronics adapted to digitize and process the data using an appropriate algorithm, such as that described herein. For instance, the report may include an estimate of the number of hard keratin (mammalian hair, feathers, etc.)-bearing pixels or objects in the assayed area, space or region.

The method of the present invention may also include the step of transmitting data relating to the approximate amount of hard keratin (mammalian hair, feathers, etc.) in an area to a site remote from the site where the measurement takes place. This may be done using any transmission method, including land line or wireless transmission. This is also used advantageously where the reflected light is sensed remotely by aircraft, satellite, boat or buoy. Processing of the data may take place at the site of light uptake or may be carried out at a remote location after transmission of the raw data. The estimated hard keratin (mammalian hair, feathers, etc.) report may be sent to public authorities, such as police departments, fire and rescue departments or life guard services to warn swimmers, boaters, sportsman or the public at large that a given body of water, or portion thereof, likely contains elevated/dangerous levels of hard keratin (mammalian hair, feathers, etc.).

The invention also includes an apparatus for determining the presence of hard keratin (mammalian hair, feathers, etc.) from light reflected therefrom, the device comprising: (a) a measurement device adapted to measure reflected light from the assayed area, space or region, the measurement comprising a measurement of the respective amount of light in one or more wavelength ranges; and (b) a processor capable of relating the approximate amount of hard keratin (mammalian hair, feathers, etc.) in an area to the respective amounts of light in different wavelength regions by applying an algorithm relating the respective amounts of light in the at least five frequency ranges to the amount of hard keratin (mammalian hair, feathers, etc.) in the assayed area, space or region.

It is preferred that the apparatus is capable of performing the algorithmic determination of the indicative portions of the reflected spectrum indicating the presence and/or quantity of hard keratin (mammalian hair, feathers, etc.) relatively quickly such that application appropriate displays or signaling can occur.

The apparatus may additionally include a report generator adapted to generate and/or store a report of the approximate percentage of the assayed area, space or region covered by hard keratin (mammalian hair, feathers, etc.) objects and/or generate and/or store images of the detected objects. Such a report generator may be any device that is adapted to place the data into a tangible medium, such as a printer, CD burner, flash memory, magnetic storage media, etc.

The apparatus may additionally include a transmitter and/or receiver adapted to transmit and/or receive and/or store data relating to the approximate amount of hard keratin (mammalian hair, feathers, etc.) in an area, and/or transmit, receive and/or store images of the detected objects from the processor to a site remote from the site where the measurement takes place. Such a transmitter may include those adapted to send, receive and/or store data such as through land line or wireless transmission, including telephone, internet, cell phone, radio, internet protocol and the like, and related or associated receiving and storage devices.

The measurement device may be any device adapted to sense and record and/or transmit the light wavelengths described above. Examples include photosensors, cameras, digital cameras and video cameras, etc.

The processor may be any data processing device having programming instructions for applying the algorithm, such as preferably a microprocessor.

It is preferred that the algorithm comprises a relationship adapted to determine the presence or absence of certain spectral features indicative of hard keratin (mammalian hair, feathers, etc.) in an area.

The measurement and/or imaging device of the present invention may be placed in any position from which it can sense the required light wavelengths (and optionally image objects), such as on a tower, pole, building or other grounded support, buildings, walls, fences or other barriers, a boat, a light house or similar dedicated tower structure, an elevated lifeguard house or guardhouse or vehicle. This will depend upon the desired application and the desired field of view and area or region to be covered, as well as the desired sensitivity and desired image generating capability. The present invention includes such things bearing, comprising or supporting a device of the present invention.

The present invention also includes measurement and/or imaging devices that may be in the form of a handheld device, such as a camera connected to a processor for processing the sensed or recorded light wavelengths for sensing, analysis and/or imaging of those measurements. The device may also be in the form of a device similar to a personal digital assistant with light sending and/or recording and processing functions.

Another variation of the present invention is a system using transmission of light measurement data to a processor at a different location, recognizing that the processing and/or imaging may be done at a different location than the light sensing/recording/imaging.

In general terms, this variation is a system for determining the presence of hard keratin (mammalian hair, feathers, etc.) from light reflected therefrom, the device comprising (a) a measurement device adapted to measure reflected light from the assayed area, space or region, the measurement comprising a measurement of the respective amount and (b) a processor at the remote site and capable of relating the approximate amount of hard keratin (mammalian hair, feathers, etc.) in an area to the respective amounts of light by applying an algorithm relating the respective amounts of light at different wavelengths to the amount of hard keratin (mammalian hair, feathers, etc.) in the assayed area, space or region, and/or of imaging objects containing hard keratin.

The invention also includes a method of developing an apparatus for determining the presence of hard keratin (mammalian hair, feathers, etc.) from light reflected therefrom, the device comprising (a) obtaining a measurement of reflected light from the assayed area, space or region, the measurement comprising a measurement of the light; (b) developing and/or applying an algorithm relating the respective amounts of light to the amount of hard keratin (mammalian hair, feathers, etc.) in an area through a determination of the presence of indicative characteristics in the target wavelength region; (c) producing a processor capable of relating the presence and/or approximate amount of hard keratin (mammalian hair, feathers, etc.) and/or imaging keratin-comprising objects in an area space or region to the presence of indicative characteristics in the target wavelength region; and (d) providing a measurement device adapted to measure reflected light from an area and adapted to provide data relating to the measurement to the processor.

The invention also includes a system using an algorithm for converting the multispectral signals into images showing the relative position of objects bearing or comprising keratin, primarily hard keratin such as mammalian hair or feathers and the like. The preferred algorithm(s) determine the presence of one or more local spectral maxima and/or minima in the near infrared range, although other algorithms may be used to determine change in slope in the spectral curve(s).

As used herein, multispectral radiation refers to light or other electromagnetic radiation of two or more different wavelengths, and spectral reflectance refers generally to a plot of reflectance versus wavelength.

The method of the present invention may be carried out using any appropriate infrared light sensing devices adapted to capture the algorithm-relevant frequencies or wavelengths as described herein, including satellites, surface sensors, and vehicle-borne sensors.

An algorithm in accordance with the present invention may be carried out by computer instructions for producing a particular type of image that can be used to identify and/or map a particular substance from a remote sensing platform in space, in an aircraft, from a vehicle or on the ground. Such algorithms may be any that are capable of determining the presence of spectral characteristics, such as those described herein.

The present invention may also include a hyperspectral imaging system adapted to perform the functions of the present invention in terms of the collection filtering and display of images. The functional aspects of the present invention may be incorporated into hyperspectral imaging systems, such as those described in U.S. Pat. Nos. 7,149,366, 7,013,172, 6,998,614, 6,734,966, 6,504,943, 6,495,818 and 6,008,492, which are hereby incorporated herein by reference.

The present invention may also be used in conjunction with night vision and/or other sensor and vision technology to determine the presence and/or position of keratin-comprising objects while also determining the presence and/or position of heat sources.

In order to identify the keratin-indicative spectral features, one may use any algorithmic or other means. Examples include the use of one or more computer programs to carry out calculations designed to detect representative spectral features within the near IR region, such as those described herein.

Because the methods and apparatus of the present invention may detect humans (living or non-living), animals (including mammals and/or birds; living or non-living) or objects made from mammals and/or birds, such as wool clothing, fur, feathers etc., the invention lends itself to a wide variety of uses where the detection and characterization of living or non-living mammals, birds or humans or objects otherwise comprising hard keratin, such as fabrics, clothing, fur, etc., regardless of environmental conditions, are desirable. These uses will be readily appreciated by one of ordinary skill in view of several examples.

The methods and apparatus of the present invention may serve a wide variety of applications, such as for the detection of animals and humans for hunting, search and rescue, security and transportation safety purposes. The present invention may be used to sense, locate or map deer or other mammals, birds or humans for hunting, driving hazards, search and rescue or similar purposes.

The present invention may be used by hunters to determine the presence and/or position of living game animals or birds. It may also find application in the location of downed prey, even prey that has expired, such that quarry can be located even after considerable time has passed. The method and system of the present invention may also be used to distinguish between aviary and mammalian prey owing to the differences between their spectral characteristics, as described herein.

Another potential application of the present invention is in the field of personal safety, wherein the method of the present invention may be used in a wide variety of security and alarm systems to protect persons and property from intrusion. The present invention may be used to detect the presence of humans or animals in areas or buildings where access is to be restricted.

The present invention may be used to detect the presence of humans or animals even in situation and environments where night vision or other detectors may not be able to function as effectively. In this same regard, the invention may be used to detect the presence of persons or animals near vehicles or their paths, such as by having devices onboard automobiles, along roadways, onboard aircraft, along runways, or on or around structures, such as windmills to detect birds.

For instance, the present invention may be used as an onboard system to detect animals (living or non-living) in a vehicle's path, such as a child behind a car or a deer, dead or alive, near or in a roadway. The invention may also be used in the form of an array of detectors to monitor a roadway where animals are known to frequent. Likewise, the present invention may be used as an array of detectors to monitor a runway where birds or animals may obstruct an airplane's path, particularly upon take-off. The invention may be used to detect and warn birds around structures where they might be harmed or be harmful such as runways or windmills.

In this same regard, because the present invention is based upon the detection of material-indicative spectral features in the near infrared, it may operate even in some types of adverse weather conditions (such as through fog or light rain), and even detect target persons or animals regardless whether they exhibit a heat signature (such as in the case where the person or animal is not living), or in cases where a person is clothed but where hard keratin surfaces (such as on visible hair or clothing), are otherwise visible to the detector of the present invention.

Still another aspect of the invention is that one may use the material-indicative spectral features in the near infrared to distinguish between objects, such as, for instance between mammals and birds. As can be appreciated from FIG. 2, the reflectance curves of the birds can be distinguished from that of other mammalian animals. This may be done through any method, including through the use of algorithms adapted to distinguish between the reflectance magnitude at points along the curve where they vary in magnitude, or by comparing reflectance values at multiple points to calculate differences in curve characteristics, such as absolute changes in magnitude, changes in slope(s), etc. As an example, one may compare reflectance values at different wavelengths, such as at about 1350 nm and about 2115 nm in FIG. 2, which comparison allows one to distinguish between hair and feathers. This might also be accomplished through application of existing techniques such as spectral matching technologies, such as spectral angle mapping, spectral feature fitting and spectral match fitting, which usually involve comparison of entire portions of spectral curves to known curves stored in memory, although these techniques generally require more computer memory to store an entire spectrum portion, as well as typically greater computing power in order to compare an entire spectrum or portion thereof.

Accordingly, the present invention may additionally comprise the step of determining whether feathers are present in the area based upon the identification of at least one spectral characteristic that is indicative of the presence of feathers.

The present invention may also include the step of distinguishing between objects comprising mammalian hair and objects comprising feathers within the region.

It will be appreciated that each of the steps, elements, features and characteristics of the present invention described herein may be combined independently with one another to achieve the benefits of each such step, element, feature or characteristic, and their combination.

Although described herein with respect to the detection of a live animal, it will be understood that the present invention includes within its scope the general detection methods and apparatus, alarm and display methods and associated apparatus, and corresponding methods and apparatus for these other uses as described herein and as otherwise will be apparent in light of the many advantages of the present invention.

BRIEF DESCRIPTION OF THE DRAWINGS

Novel features and advantages of the present invention, in addition to those mentioned above, will become apparent to those skilled in the art from a reading of the following detailed description in conjunction with the accompanying drawings summarized as follows.

DETAIL DESCRIPTION OF PREFERRED EMBODIMENT(S)

The preferred system herein described is not intended to be exhaustive or to limit the invention to the precise forms disclosed. They are chosen and described to explain the principles of the invention and the application of the method to practical uses so that others skilled in the art may practice the invention.

Figure 1:
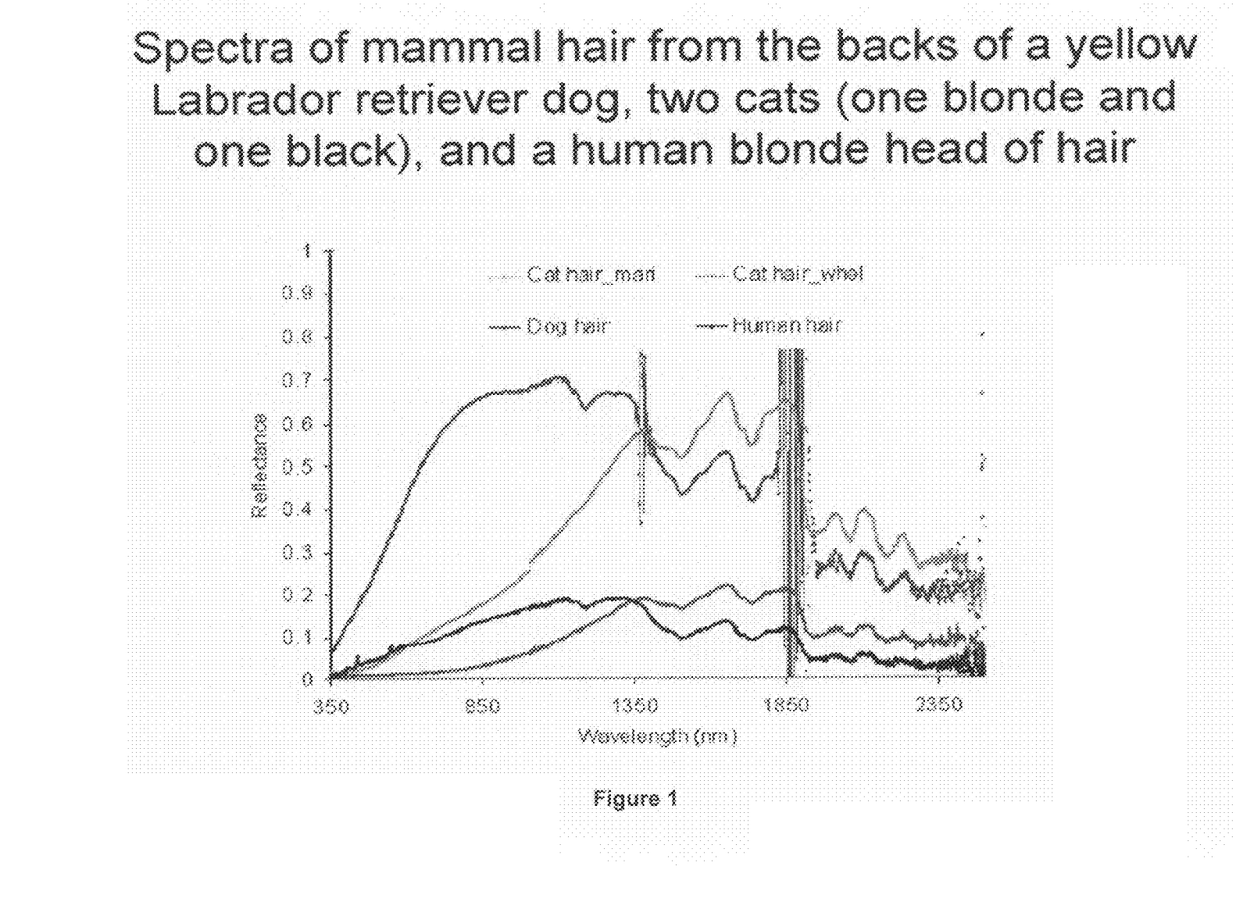
FIG. 1 is a graph of reflectance versus wavelength showing the spectra of hard keratin (mammalian hair, feathers, etc.) from a variety of sources, as may be applied in accordance with one embodiment of the present invention.

Referring to FIGS. 1 and 2, the present invention may take advantage of the distinctive pattern(s) and/or spectral feature(s) in the near infrared reflectance absorption band that are shown to be indicative of the presence of hard keratin from a variety of sources. FIGS. 1 and 2 show the presence of distinctive pattern(s) and/or spectral feature(s) in the near infrared reflectance absorption band, that may be used as a basis for the methods and apparatus of the present invention which generally involves the detection of one or more of these hard keratin-indicative pattern(s) and/or spectral feature(s) in the near infrared reflectance absorption band.

FIG. 1 shows reflectance profiles from light reflected from several mammals, including a yellow Labrador retriever, a blonde cat, a black cat and the hair of a blonde human. As can be appreciated from these reflectance profiles, each profile exhibits similar character and structure above about 1350 nm, more specifically between about 1350 nm and about 2350 nm.

For further clarification, FIG. 1 shows the following spectral features:

| Spectral Feature Reference | Wavelength (nanometers range) | Spectral Feature Type |
|---|---|---|
| A | 1500 ± 50 | Maximum |
| B | 1650 ± 50 | Minimum |
| C | 1725 ± 50 | Maximum |
| D | 1850 ± 50 | Minimum |
| E | 1900 ± 50 | Maximum |
| F | 1950 ± 50 | Minimum |
| G | 2000 ± 50 | Maximum |
| H | 2050 ± 50 | Minimum |
| I | 2125 ± 50 | Maximum |
| J | 2175 ± 50 | Minimum |
| K | 2250 ± 50 | Maximum |

In a more preferred embodiment, the at least one absorbance maximum and/or minimum may be selected from one or more of the following distinctive pattern(s) and/or spectral feature(s) in the near infrared reflectance absorption bands:

| Spectral Feature Reference | Wavelength (nanometers range) | Spectral Feature Type |
|---|---|---|
| A | 1500 ± 50 | Maximum |
| B | 1650 ± 50 | Minimum |
| C | 1725 ± 50 | Maximum |
| D | 1850 ± 50 | Minimum |

Figure 3:
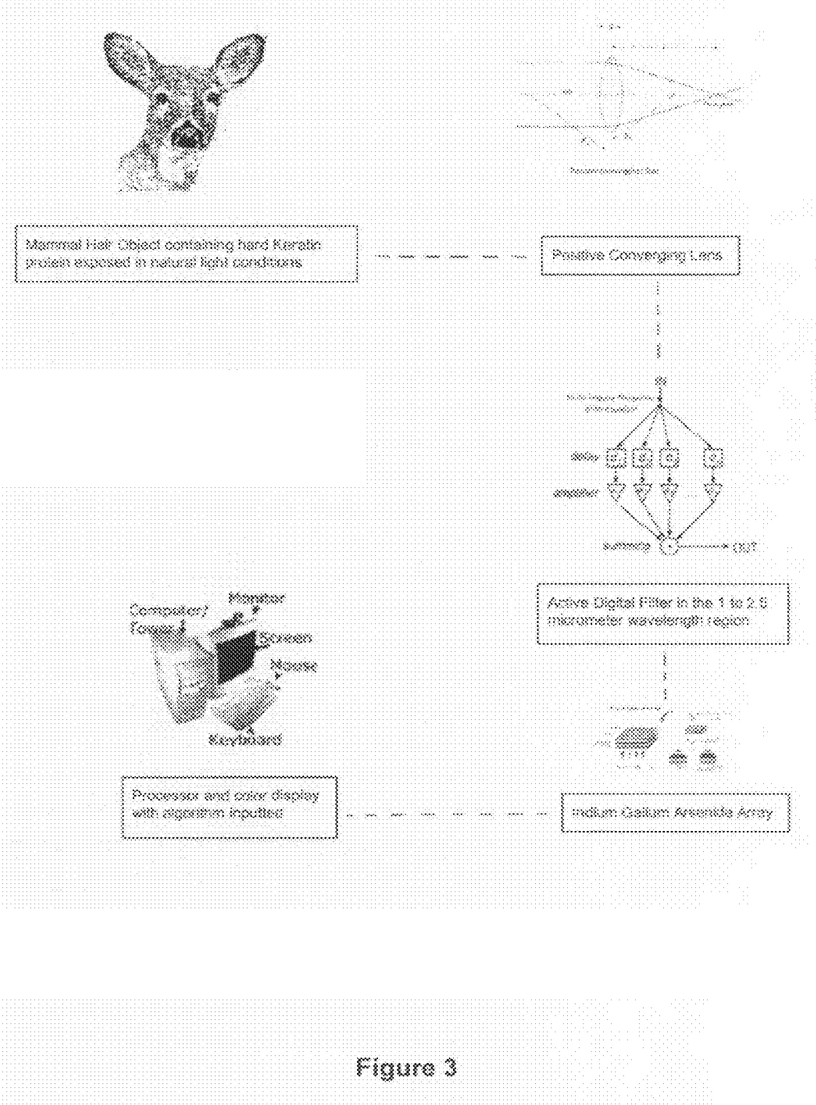
FIG. 3 is a schematic showing an example of the steps or a method in accordance with one embodiment of the present invention.

FIG. 3 is a schematic showing an example of the steps or a method in accordance with one embodiment of the present invention. FIG. 3 shows light (from ambient or active source), being reflected and captured from an object comprising hard keratin, such as a deer bearing mammalian hair. The light reflected from the keratin surface is collected by an appropriate collection device, such as a positive converging lens which focuses the light through an active digital filter in the 1.0 to 2.5 micrometer range. The filter light is directed to an indium gallium arsenide array adapted to measure the intensity of the light along the 1.0 to 2.5 micrometer range. The measured intensities are in term directed to a processor, such as computer microprocessor, which contains program instructions to determine the presence of pixels wherein the presence of keratin is indicated.

Any of the identified maxima or minima, combinations thereof, or any other spectral feature(s) described herein or that might otherwise be identified as distinctive of hard keratin, may be used as a basis of the methods and apparatus of the present invention.

The present invention includes the use of algorithms developed to measure relative hard keratin, such as exists in mammalian hair, feathers and the like, and objects comprising this/these material(s).

For instance, in one embodiment of the invention, it has been found that the hair on a living dog, the hair on two cats, and the hair on a human head has a similar absorption band (i.e., a spectral feature) centered near a wavelength of 1.513 micrometers. The present invention therefore correspondingly includes an imaging device adapted to employ at least three spectral bands centered around 1.359 micrometers (Band 1), centered around 1.513 micrometers (Band 2), and 1.664 micrometers (Band 3) that will be able to image mammal hair, if the bandwidths are fairly narrow (around 0.01 micrometer wide, depending upon signal-to-noise ratio), so as to be able to ascertain the existence of the spectral feature near 1.513 micrometers (Band 2). One algorithmic processing method may be to use a three-band ratio of (B1+B3)/[2*(B2)] that, when turned into an image, would make mammal hair bright and almost everything else (maybe nothing else) appear medium gray or darker.

For instance, the spectral bands centered around 1.359 micrometers (Band 1), 1.513 micrometers (Band 2), and 1.664 micrometers (Band 3) would be analyzed by sampling the reflectance at wavelengths just above or just below these wavelengths to determine the existence, in this case, of a local absorbance minimum centered around 1.513 micrometers (Band 2). In such a case, the device uses filters to sample the reflectance for a small wavelength range extending from just above to just below each assay point. For instance, to measure reflectance at 1.359 micrometers, one may measure the average reflectance within a range from about 1.349 micrometers to about 1.359 micrometers.

Applying the algorithm (B1+B3)/[2*(B2)], this value will be >1.0 where a local reflectance minimum exists, and <1.0 where a local reflectance maximum exists.

It will be appreciated that any one or more of the local reflectance minima or maxima identified herein may be the chosen as the target wavelength(s) for algorithmic treatment. In the case of multiple spectral features, it will be appreciated that one may use readings at various regions along the spectral curve in order to identify such spectral features by reference to the same region in some instances. For instance, one may identify two spectral features by using readings at points B1, B2 and B3, and by using points B3, B4 and B5, where the spectral features are located at B2 and B4.

The system of the present invention may be constituted using a commercially available near infrared imaging spectrophotometer, such as those commercially available from AutoVision/SpecTIR, LLC of Oulu Finland; Flux Data Incorporated of Rochester, N.Y.; Tetracam Inc. of Chatsworth Calif.; and Photonics OnLine at http://www.photonicsonline.com.

Their present invention may be adapted for a wide variety of uses in any application where the presence or absence of keratin, and/or detection or imaging of objects comprising kertain, such as by using an imager of the present invention: (1) as a hunter's aid (particularly for hunters with poor vision) to locate and/or distinguish by type live or downed prey; (2) as an automobile automatic warning that at least one mammal, bird or other object comprising hard keratin is in the path of a vehicle (e.g., children or deer); (3) as a search-and-rescue device, to determine or confirm the presence of mammals and/or humans and/or birds, and infer whether or not it is human and/or animal and/or bird by the size, shape and/or motion of the identified objects comprising hard keratin within the sensed region or area.

Figure 4:
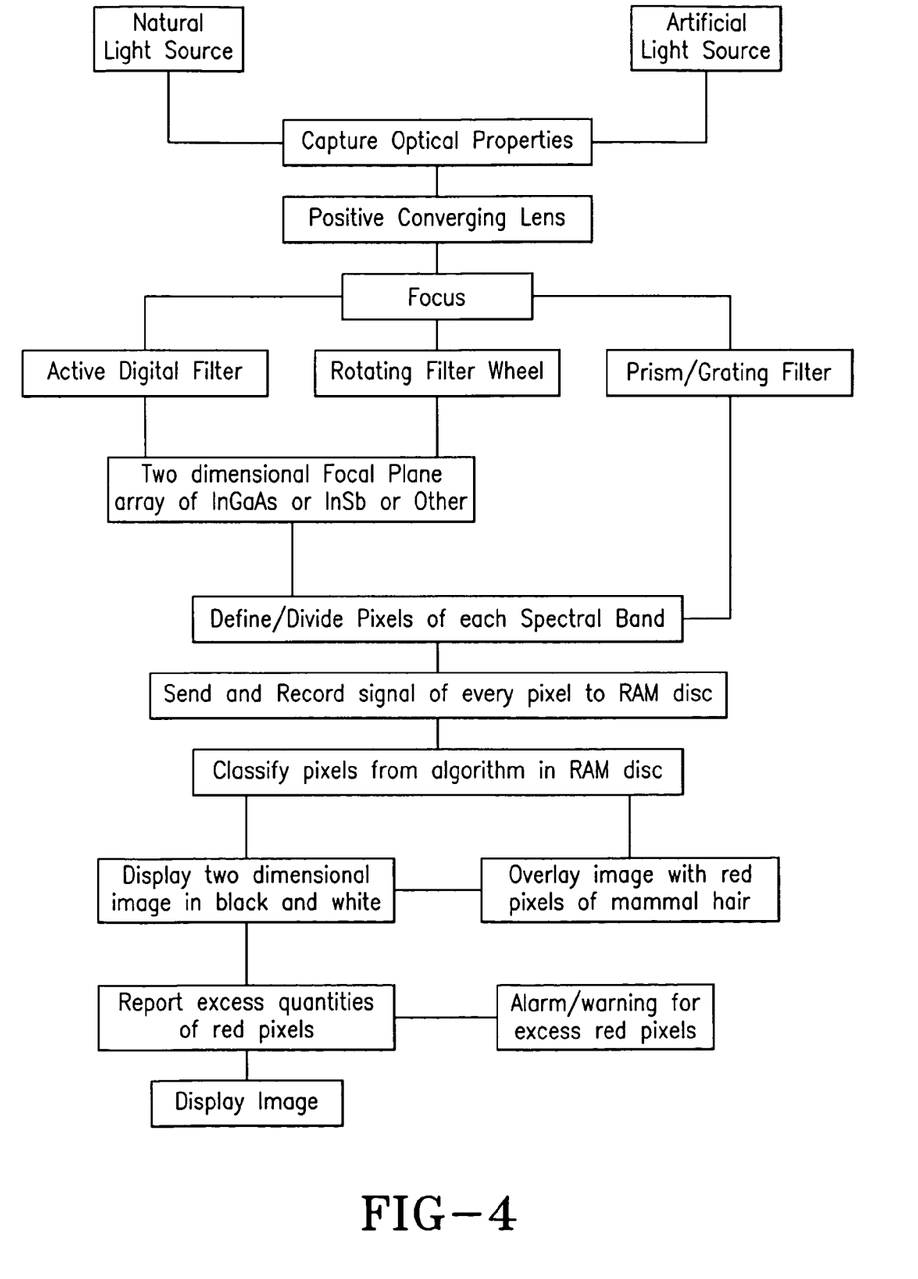
FIG. 4 is a schematic showing a number of variations of the method of the present invention, representative of several embodiments of the present invention.

The schematic of FIG. 4 shows a number of variations of the present invention. FIG. 4 shows that the method and apparatus of the present invention can be based upon the use of natural or artificial light.

The artificial light may be in the form of one or more infrared lasers that may be directed in a pattern, such as a raster pattern, to illuminate the area of interest with light in the near infrared range. This may be done from a hand-held device, a fixed light source (such as on a building, post, tower or wall) or from a vehicle, such as an automobile, boat, aircraft (helicopter or airplane) or even from a satellite.

The optical properties of the light are collected and the light is focused, such as through a positive converging lens. The light may be filtered in any functionally appropriate way in view of the requirements of the invention with respect to wavelength region selection, such as through an active digital filter, a rotating wheel filter or a prism or grating. After emerging from either filter, the light is directed to a two dimensional focal plane array of indium gallium arsenide, indium antimony, or other sensing material adapted to measure the intensity of light of the wavelengths in the near and short wave infrared range. Each pixel is divided and defined for each spectral band in the near and short wave infrared range. The signal of every pixel is sent to a storage medium, such as a RAM disc. Each of the pixels is then classified through the application of one or more algorithms adapted to determine the presence of one or more distinctive spectral features, such as an reflectance minima and/or maxima. The image of the two dimensional array may be displayed as a background image, such as a black and white image. The present invention may also incorporate the use of a split display displaying active response from inactive/background.

Combined with the background image is an image that is created from those pixels wherein the presence of one or more distinctive spectral features is determined by the processor (indicator pixels). These pixels may be directed by the program to be colored or otherwise altered so as to be visually distinguishable from the background image.

As an alternative, the processor may also determine the number or statistical distribution of the indicator pixels and, where that number or statistical distribution exceeds a threshold amount, an alarm or some other action is caused as a result of that determination, such as a signal or recordation.

As still another alternative, spatial imaging techniques may be applied to construct an image from the individual pixel measurements by virtue of the comparison of the individual measurements in neighboring pixels, one to the other, in order to construct and display an image.

The approximate distance-relative pixel size may be set depending upon the desired application, taking into account typical operating distances from the target, the nature of the target, the degree to which, and rate at which the target may move, and the degree to which and how the target may be obstructed.

Because one may select a spectral region and algorithm to create high contrast between target and background, one may use larger pixel sizes and still detect the target, compared with having to detect shapes and appendages of a target, which requires pixel sizes smaller than the appendages. For instance, the mere detection of birds along an airport runway might only require one meter square pixels for this high-contrast multispectral algorithm, whereas methods of detecting birds by their shapes, necks, beaks, etc. would require pixels smaller than the necks and beaks (less than 1 cm). Because there is always a limit to how many pixels can be detected, relayed and stored per second, the multispectral sensor (with multispectral algorithm) can cover much more area than a shape-detector (or segmentation) sensor, though both are reporting back on the same number of pixels in the same time period. The pixel sizes are much larger for the multispectral sensor than for the shape-detector sensor, and may do the job more accurately, because spectral features are usually more unique characteristics than are shapes and sizes, especially in the case of mammal hair and feathers versus shapes of mammals and birds.

Likewise, to detect partially obstructed responsive target objects, such as by being able to detect smaller portions of partially obscured responsive target objects that might be visible though brush, the multispectral sensor with the multispectral algorithm described above would be superior to a segmentation algorithm because it would not matter what the shapes of the mammal or bird patches were that were visible through the brush, only that up to half a pixel is filled (in whatever number of patches) by mammal hair or feathers.

Figure 5:
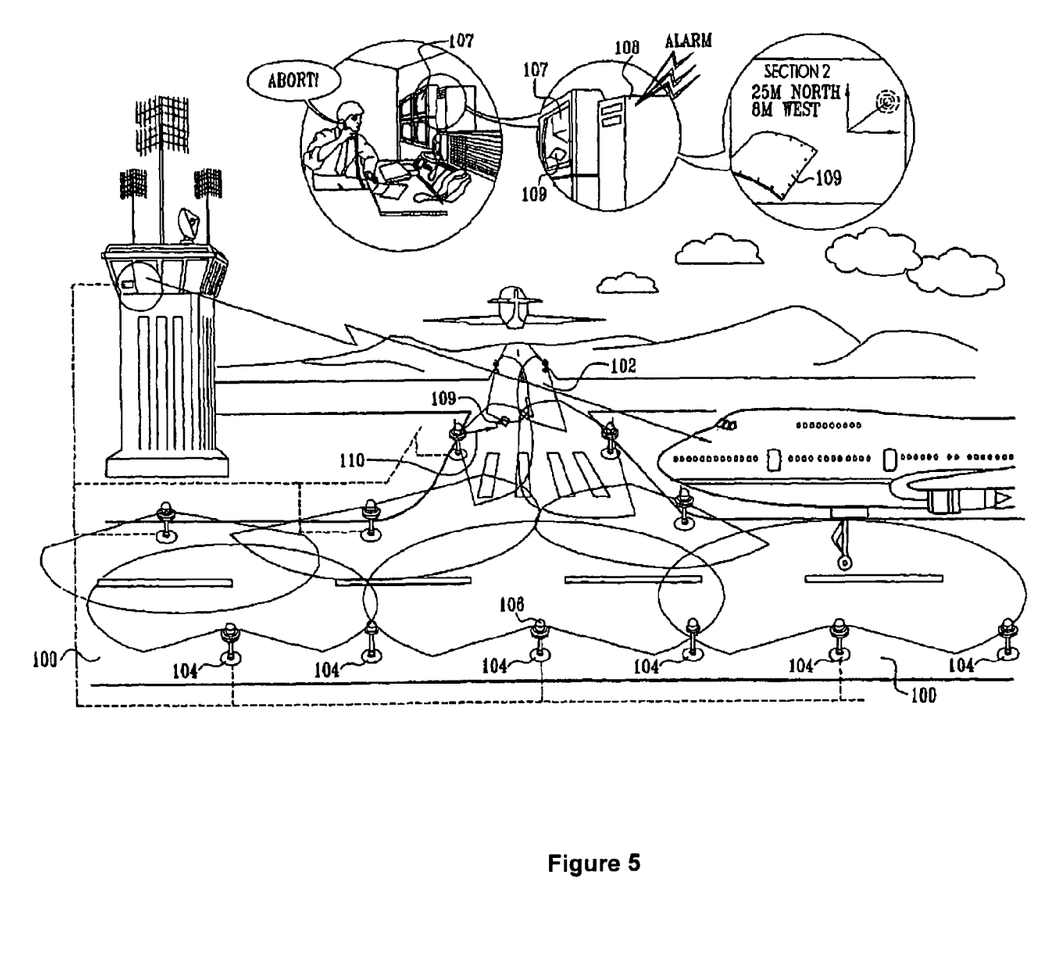
FIG. 5 is a schematic view of an airport monitoring system in which the apparatus and methods of the present invention may be used, in accordance with one embodiment of the present invention.

As an example of the use of the invention for safety and security purposes, FIG. 5 shows how devices in accordance with the present invention might be placed around runways or airport grounds to provide a visual indication of the presence of birds, animals or unauthorized personnel. The device of the preset invention may be readily incorporated into existing security and detection schemes, such as those described in U.S. Pat. Nos. 7,253,748, 7,223,047 and 4,989,084 which are hereby incorporated herein by reference.

FIG. 5 shows how a runway 100 may be monitored and protected by having a number of detector positions 104 that are provided with detectors such as 106 that are positioned so as to monitor areas of an airport runway as shown, such as area 102. The monitored areas or regions may also include regions of space around the runway, such as in the flight path to detect birds, or alongside the runway to detect animals. The detectors may be situated to detect the presence of a keratin-bearing object, such as object 109, along vector 110.

In the event an object comprising keratin 109 is detected, an image and/or alarm signal can be sent to a microprocessor 108 that may issue an alarm signal and/or show a display of object 109 in image display 107.

Having shown and described a preferred embodiment of the invention, those skilled in the art will realize that many variations and modifications may be made to affect the described invention and still be within the scope of the claimed invention. Thus, many of the elements indicated above may be altered or replaced by different elements which will provide the same result and fall within the spirit of the claimed invention. It is the intention, therefore, to limit the invention only as indicated by the scope of the claims.

What is claimed is:

1. A method comprising the steps of: (a) sensing with a sensor unit reflected light in the short wave infrared wavelength region from objects in an area said area comprising at least one first object bearing hard keratin and second objects bearing no keratin; and (b) determining whether hard keratin is present in said area based upon the identification of at least one spectral characteristic in said reflected light from said at least one first object, which spectral characteristic is not found in said second objects, that is indicative of the presence of hard keratin, so as to distinguish at least one first object from said second objects within said area.

2. A method according to claim 1 wherein the identification of at least one spectral characteristic in said reflected light from said at least one first object that is indicative of the presence of hard keratin comprises the identification of at least one local minimum in the short wave infrared wavelength region, which does not appear in said reflected light from said second objects.

3. A method according to claim 2 wherein said determination step includes identifying at least two reflectance minima in the short wave infrared wavelength region that are indicative of the presence of hard keratin which do not appear in said reflected light from said second objects.

4. A method according to claim 2 wherein said determination step includes identifying at least three reflectance minima in the short wave infrared wavelength region that are indicative of the presence of hard keratin, which do not appear in said reflected light from said second objects.

5. A method according to claim 1 wherein the identification of at least one spectral characteristic in said reflected light from said at least one first object that is indicative of the presence of hard keratin comprises the identification of at least one local maximum in the short wave infrared wavelength region, which does not appear in said reflected light from said second objects.

6. A method according to claim 1 wherein the identification of at least one spectral characteristic in said reflected light from said at least one first object that is indicative of the presence of hard keratin comprises the identification of at least one reflectance minimum in the short wave infrared wavelength region, which does not appear in said reflected light from said second objects.

7. A method according to claim 6 wherein said at least one reflectance minimum in the short wave near infrared wavelength region is in the range of from about 1400 nanometers to about 2300 nanometers.

8. A method according to claim 1, wherein said determination generates data, and additionally comprising creating a visual display so as to display said at least one first object in said area.

9. A method according to claim 8, wherein said determination generates data from a scan of said area indicating the presence of said at least one first object in said area and the presence of non-hard keratin objects in said area, and additionally comprising creating a visual display of said area so as to distinguish said at least one first object from said second objects in said area.

10. A method according to claim 9, additionally comprising determining the heat signature of said at least one first object and said second objects in said area, and additionally comprising displaying the heat signature of said at least one first object and said second objects in said area.

11. A method according to claim 1 wherein step (b) includes determining whether feathers are present in said area based upon the identification of at least one spectral characteristic that is indicative of the presence of feathers.

12. A method according to claim 11 additionally comprising the step of: (d) distinguishing between objects comprising mammalian hair and objects comprising feathers within said region.

13. A method according to claim 1 wherein said sensor unit is mounted on a vehicle, wherein said vehicle is selected from the group consisting of aircraft, automobiles, satellites, boats and buoys.

14. A method according to claim 1 wherein said sensor unit is mounted on a structure, wherein said structure is selected from the group consisting of towers, poles, buildings, walls, windmills and fences.

15. A method according to claim 1 wherein said area is an outdoor area.

16. A method comprising the steps of: (a) exposing with a light source an area, said area comprising at least one first object bearing hard keratin and second objects bearing no keratin, said light source emitting light in the short wave infrared wavelength region; (b) sensing with a sensor unit reflected light from said area; and (c) determining whether hard keratin is present in said area based upon the identification of at least one spectral characteristic in said reflected light from said at least one first object, which spectral characteristic is not found in said second objects, that is indicative of the presence of hard keratin, so as to distinguish at least one first object from said second objects within said area.

17. A method according to claim 16 wherein the identification of at least one spectral characteristic in said reflected light from said at least one first object that is indicative of the presence of hard keratin comprises the identification of at least one local minimum in the short wave infrared wavelength region, which does not appear in said reflected light from said second objects.

18. A method according to claim 17 wherein said determination step includes identifying at least one reflectance minimum in the short wave infrared wavelength region that is indicative of the presence of hard keratin, which does not appear in said reflected light from said second objects.

19. A method according to claim 17 wherein said determination step includes identifying at least two reflectance minima in the short wave infrared wavelength region that are indicative of the presence of hard keratin, which do not appear in said reflected light from said second objects.

20. A method according to claim 17 wherein said determination step includes identifying at least three reflectance minima in the short wave infrared wavelength region that are indicative of the presence of hard keratin, which do not appear in said reflected light from said second objects.

21. A method according to claim 16 wherein the identification of at least one spectral characteristic in said reflected light from said at least one first object that is indicative of the presence of hard keratin comprises the identification of at least one local maximum in the short wave infrared wavelength region, which does not appear in said reflected light from said second objects.

22. A method according to claim 16 wherein the identification of at least one spectral characteristic in said reflected light from said at least one first object that is indicative of the presence of hard keratin comprises the identification of at least one reflectance minimum in the short wave infrared wavelength region, which does not appear in said reflected light from said second objects.

23. A method according to claim 22 wherein said at least one reflectance minimum in the short wave infrared wavelength region is in the range of from about 1400 nanometers to about 2300 nanometers.

24. A method according to claim 16, wherein said determination generates data, and additionally comprising creating a visual display so as to display said at least one first object in said area.

25. A method according to claim 24, wherein said determination generates data from a scan of said area indicating the presence of said at least one first object in said area and the presence of non-hard keratin objects in said area, and additionally comprising creating a visual display of said area so as to distinguish said at least one first object from said second objects in said area.

26. A method according to claim 25, additionally comprising determining the heat signature of said at least one first object and said second objects in said area, and additionally comprising displaying the heat signature of said at least one first object and said second objects in said area.

27. A method according to claim 16 wherein step (c) includes determining whether feathers are present in said area based upon the identification of at least one spectral characteristic that is indicative of the presence of feathers.

28. A method according to claim 27 additionally comprising the step of: (d) distinguishing between objects comprising mammalian hair and objects comprising feathers within said region.

29. A method according to claim 16 wherein said area is an outdoor area.

* * * * *